United States Patent [19]

Goralski

[11] 4,070,471

[45] Jan. 24, 1978

[54] 3,4,5-TRIS(4-PYRIDINYLTHIO)-2,6-PYRIDINEDICARBONITRILE AND ITS USE TO CONTROL BACTERIA AND FUNGI

[75] Inventor: Christian T. Goralski, Midland, Mich.

[73] Assignee: The Dow Chemical Company, Midland, Mich.

[21] Appl. No.: 723,423

[22] Filed: Sept. 15, 1976

[51] Int. Cl.$^2$ .................... A01N 9/22; C07D 401/14
[52] U.S. Cl. ............................ 424/263; 260/294.8 G
[58] Field of Search ................ 260/294.8 G; 424/263

[56] References Cited

U.S. PATENT DOCUMENTS

| 2,826,586 | 3/1958 | Cislak ............................ 260/294.8 G |
| 3,325,503 | 6/1967 | Bimber ............................ 260/294.9 |
| 3,519,634 | 7/1970 | Mohr et al. ...................... 260/294.8 G |

OTHER PUBLICATIONS

Merck Index 8th Ed., 1968, p. 1226.

*Primary Examiner*—Leonard Schenkman
*Attorney, Agent, or Firm*—Daniel De Joseph; Theodore Post; C. Kenneth Bjork

[57] ABSTRACT

3,4,5-Tris(4-pyridinylthio)-2,6-pyridinedicarbonitrile is prepared by reacting three molar proportions of 4-alkali metal mercaptopyridine with one molar proportion of 3,4,5-trihalo-2,6-pyridinedicarbonitrile. The product has antimicrobial utility.

3 Claims, No Drawings

3,4,5-TRIS(4-PYRIDINYLTHIO)-2,6-PYRIDINEDICARBONITRILE AND ITS USE TO CONTROL BACTERIA AND FUNGI

SUMMARY OF THE INVENTION

This invention concerns the compound 3,4,5-tris(4-pyridinylthio)-2,6,-pyridinedicarbonitrile, hereinafter Compound, having the following formula

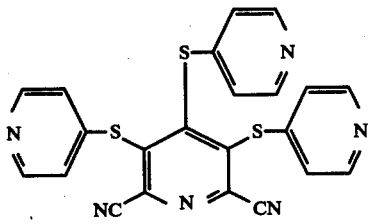

The compound is prepared by reacting substantially three molar proportions of 4-alkali metal mercaptopyridine, advantageously pyridine-4-sodium thiolate, as such or prepared in situ, with substantially one molar proportion of 3,4,5-trihalo-2,6,-pyridinedicarbonitrile, wherein halo is chloro or bromo, in the presence of a lower alkanol as reaction medium, advantageously methanol. The reaction mixture is heated to reflux and cooled. The solvent is removed in vacuo to leave the solid gummy product. Mixing of the gum with acetone, filtering off the solid and drying the latter gives the product as a yellow to orange powder. The latter may be recrystallized from absolute ethanol to give small crystals, melting at 186°-189° C with decomposition.

DESCRIPTION OF THE PREFERRED EMBODIMENTS

The following additional description and example further describe the invention and the manner and process of making and using it to enable the art skilled to make and use the same and set forth the best mode contemplated by the inventor of carrying out the invention.

The compound of this invention has antimicrobial utility. In a conventional in vitro agar Petri dish dilution test for determining activity against bacteria and fungi, the minimum inhibitory concentration (MIC) in parts per million (ppm) against the following organisms was found:

| MIC, ppm, of Compound of Example | |
|---|---|
| S. aureus | 100 |
| T. mentagrophytes | 100 |
| B. subtilis | 100 |
| A. terreus | 100 |
| P. pullulans | 100 |
| M. phlei | 10 |
| Ceratocystis IPS | 100 |
| Cephaloascus fragans | 100 |
| Trichoderm. Sp. Madison P-42 | 100 |

In accordance with the present invention, Compound can be employed for the control of many bacterial and fungal pests. In still further operations, Compound or compositions containing it as a toxic constituent can be included in and on plaster, ink, wallboard, textiles, paper, adhesives, soaps, synthetic detergents, cutting oils, polymeric materials, embalming fluids, oil paints and latex paints to prevent the attack of various fungal pests and the subsequent economic loss due to the degradation of such products by microorganisms. Also, Compound can be distributed in textiles or cellulosic materials to preserve and protect such products from the attack of the organisms of rot, mold and decay.

The exact concentration of the toxicant to be employed in the treating compositions is not critical and may vary considerably provided the required dosage of the effective agent is supplied in the ink, adhesive, soap, cutting oil, polymeric material, paint, textile, paper, or growth medium. The concentration of toxicant in liquid compositions generally is from about 0.0001 to 50 percent by weight. Concentrations up to 95 percent by weight are oftentimes conveniently employed, particularly in concentrate compositions. In dusts, the concentrations of the toxicant can be from about 0.1 to 95 percent by weight. In compositions to be employed as concentrates, the toxicant can be present in a concentration of from 5 to 98 percent by weight. For use as a spray, it is often convenient to apply the Compound as a wettable powder.

EXAMPLE 3,4,5-Tris(4-pyridinylthio)-2,6-pyridinedicarbonitrile

In a 500 ml single-neck flask equipped with a magnetic stirrer and a reflux condenser fitted with a calcium chloride drying tube were placed 250 ml of methanol and 2.30 g (0.10 mol) of sodium metal. After all of the sodium had reacted, 11.11 g (0.10 mol) of 4-mercaptopyridine was added and the solution was allowed to stir for five minutes. To the resulting thiolate solution, 7.65 g (0.033 mol) of 3,4,5-trichloro-2,6-pyridinedicarbonitrile was added. The reaction mixture immediately became cloudy and orange in color. The reaction mixture was heated to reflux and then cooled. The methanol was removed in vacuo leaving a red-orange gum. Mixing of the gum with acetone, filtering off the solid and drying the latter afforded 6.89 g of the title compound as a yellow to orange powder, m.p. 186°-189° C (dec.). A 1.00 g sample was recrystallized from absolute ethanol to give a 0.25 g analytical sample as small, yellow-orange crystals, m.p. 186°-189° C (dec.). Anal. % Calcd. for $C_{22}H_{12}N_6S_3$: C, 57.87; H, 2.65; N, 18.41. Found: C, 57.64; H, 2.59; N, 18.22.

The procedure of the example, substituting 3,4,5-tribromo-2,6-pyridinedicarbonitrile for the given 3,4,5-trichloro analog gives exactly similar results.

Preparation of Starting Materials

The trihalopyridinedicarbonitrile starting materials can be prepared by the method of U.S. Pat. No. 3,325,503 as to the polychloro compound. The tribromo analog is prepared from the trichloro compound by the method described in U.S. Pat. No. 3,732,234, Column 16, under "Preparation of Starting Materials". The 4-mercaptopyridine starting material is a commercial product, available inter alia from Aldrich Chemical Company, Inc.

What is claimed is:
1. The compound 3,4,5-tris(4-pyridinylthio)-2,6,-pyridinedicarbonitrile.
2. A method for controlling bacteria and fungi which comprises applying to said bacteria and fungi or their habitat an antimicrobially effective amount of 3,4,5-tris(4-pyridinylthio)-2,6-pyridinedicarbonitrile.
3. A composition for controlling bacteria and fungi comprising an antimicrobially effective amount of 3,4,5-tris (4-pyridinylthio)-2,6-pyridinedicarbonitrile in combination with a solid or liquid diluent medium.

* * * * *